(12) United States Patent
Mamine et al.

(10) Patent No.: US 7,371,532 B2
(45) Date of Patent: May 13, 2008

(54) METHOD AND APPARATUS FOR DETERMINING BASE SEQUENCE OF NUCLEIC ACID MOLECULE

(75) Inventors: Takayoshi Mamine, Kanagawa (JP); Atsumi Tsujimoto, Tokyo (JP); Takuro Yamamoto, Kanagawa (JP)

(73) Assignee: Sony Corporation, Tokyo (JP)

( * ) Notice: Subject to any disclaimer, the term of this patent is extended or adjusted under 35 U.S.C. 154(b) by 109 days.

(21) Appl. No.: 11/231,998

(22) Filed: Sep. 22, 2005

(65) Prior Publication Data

US 2006/0115833 A1 Jun. 1, 2006

(30) Foreign Application Priority Data

Sep. 28, 2004 (JP) .......................... P2004-281000

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3
(58) Field of Classification Search .............. 435/6; 536/23.1, 24.3
See application file for complete search history.

(56) References Cited

U.S. PATENT DOCUMENTS 6,074,823 A * 6/2000 Koster .................. 435/6

FOREIGN PATENT DOCUMENTS

| JP | 6245754 | 6/1994 |
|----|---------|--------|
| JP | 2004-16171 | 1/2004 |
| JP | 2004-125706 | 4/2004 |

OTHER PUBLICATIONS

Saiki et al., Enzymatic Amplification of β-genomic sequences and restriction site analysis for diagnosis of sickle cell anemia. Science 230 : 1350-1354(1985).*

Chehab et al. Detection of sickle cell anaemia and thalassemias. Nature 329 : 293-294 (1987).*

* cited by examiner

*Primary Examiner*—Ethan Whisenant
(74) *Attorney, Agent, or Firm*—Finnegan, Henderson, Farabow, Garrett & Dunner, L.L.P.

(57) ABSTRACT

Disclosed herein is a method and apparatus for determining the base sequence of a nucleic acid molecule by cleaving a nucleic acid molecule of interest while controlling the cleavage site, measuring the change in mass which occurs in the nucleic acid molecule after the cleavage step, and acquiring the base information of the cleaved nucleic acid molecule from the data about the change in mass. The method and apparatus are based on the principle which is entirely different from that used for the conventional technique.

14 Claims, 2 Drawing Sheets

METHOD AND APPARATUS FOR DETERMINING BASE SEQUENCE OF NUCLEIC ACID MOLECULE

BACKGROUND OF THE INVENTION

The present invention relates to a technique to determine the base sequence of a nucleic acid molecule. More particularly, the present invention relates to a method and apparatus for determining the base sequence of a nucleic acid molecule on the basis of information about the change in mass of a nucleic acid molecule that has undergone cleavage.

There have recently been proposed several techniques to determine the base sequence of a nucleic acid molecule (such as DNA). Attempts are being made to carry out such techniques automatically and rapidly with higher accuracy. A brief description is given below of the major techniques to determine the base sequence.

The first one is the dideoxy sequencing method (or chain termination method or Sanger method) proposed by Sanger et al. This method is intended to determine the base sequence of a single-stranded DNA molecule. The reaction involved in this method is to synthesize a complementary DNA from Klenow fragments by using the single-stranded DNA of interest as the template in the presence of one of four species of dideoxyribonucleotide which prevents the synthesis of complete DNA but gives rise to DNA fragments varying in length. This reaction is repeated for all of the four species of dideoxyribonucleotide, and the resulting DNA fragments are separated by polyacrylamide gel electrophoresis with a resolution of one base difference. This DNA sequencing technique is considered to be suitable for the sequencing of DNA fragments each having hundreds of bases.

The second one is the whole-genome shotgun sequencing method, which is intended to determine the base sequence of long-chain DNA of genome. This method consists of cleaving all DNAs into fragments of adequate length by using a restriction enzyme, decoding the base sequence at both ends of each DNA segment, and splicing the DNA segments together at the position where the sequences overlap, by using a computer. At present, this method is used mainly for determining the base sequence of microbial genome. Incidentally, it has been reported that Celera Genomic Corp. completed the genomics of drosophila by using this method.

The third one is the clone-by-clone shotgun sequencing method, which is also intended to determine the base sequence of long-chain DNA of genome. It consists of steps of cleaving DNA into segments, determining the position of the site of cleavage by a plurality of restriction enzymes, preparing a genome DNA, and cleaving the DNA fragments into smaller fragments, thereby determining the base sequence. This method takes longer time and more labor for decoding as compared with the whole-genome shotgun sequencing method; however, it is used for humane genomics and rice genomics because of its high decoding precision.

Additional sequencing methods, which rely on the change in mass by reactions involving nucleic acids, are disclosed in Patent Documents 1 to 3 given below. Patent Document 1 is concerned with a technique to detect the change in mass that occurs when dNTP (which is supplied to the system) combines with the DNA sample by using a piezoelectric element which changes in resonance frequency in response to the change in mass, thereby detecting whether or not the primer has grown. Patent Document 2 is concerned with a technique to detect hybridization by measuring the change in characteristic frequency of a cantilever. Patent Document 3 is concerned with an instrument to read the base sequence in DNA of interest by means of a surface acoustic wave device that changes in characteristic properties when the DNA undergoes hybridization.

[Patent Document 1]
Japanese Patent Laid-open No. 2004-16171
[Patent Document 2]
Japanese Patent Laid-open No. 2004-125706
[Patent Document 3]
Japanese Patent Laid-open No. Hei 6-245754

SUMMARY OF THE INVENTION

It is an embodiment of the present invention to provide a new technique to reliably determine the base sequence of a nucleic acid molecule which is entirely different from the conventional one.

The present invention is directed to a method for determining the base sequence of a nucleic acid molecule, the method including a first step of cleaving a nucleic acid molecule of interest while controlling the cleavage site, a second step of measuring the change in mass which occurs in the nucleic acid molecule after the first step, and a third step of acquiring the base information of the cleaved nucleic acid molecule from the data measured in the second step.

Incidentally, the term "nucleic acid molecule of interest" used in the present invention denotes a nucleotide chain whose base sequence is to be decoded. The nucleic acid of interest is not limited to either the single-stranded chain or the double-stranded chain, and it is not restricted in chain length (or base number).

The method according to the present invention is based on the principle that individual nucleic acid molecules differing in base species have masses of their own and it is possible to obtain information about base species or base sequence of a nucleic acid molecule of interest from the difference ($\Delta m$) between the mass ($M_1$) of the nucleic acid molecule of interest and the mass ($M_2$) of the cleaved nucleic acid molecule, where $\Delta m = M_1 - M_2$.

According to the present invention, the above-mentioned first to third steps may be repeated as many times as necessary if the nucleic acid molecule of interest has a long nucleotide chain (e.g., oligonucleotide and polynucleotide), so that it is possible to efficiently determine the sequence of all bases in the nucleic acid of interest.

The first step for cleaving the nucleic acid molecule of interest may be accomplished by any method so long as it cleaves the nucleic acid molecule of interest at the desired site of cleavage under controllable conditions. For example, this cleavage may be accomplished by means of enzymatic decomposition reaction. To be concrete, the embodiment may be achieved by using a nuclease (such as exonuclease) that starts cleavage at the site near the terminal.

In the first step, the nucleic acid molecule of interest is cleaved sequentially by the unit of nucleotide, with cleavage starting at the site near the terminal. The change in mass after each cleavage is measured. The thus obtained data ($\Delta m$, which is the difference in mass) permits the determination of the base species and base sequence of the cleaved nucleic acid molecules.

The first step may be applied to the nucleic acid molecule of interest which retains its initial chain length without segmentation. However, the first step may also be applied to the nucleic acid molecule of interest which has been (or is being) segmented by restriction enzymes.

It is also possible to measure a plurality of segmented nucleic acids in parallel and to determine their base sequence in parallel. This will save time required for sequencing. With this technique, the base sequence of individual segmented nucleic acid molecules is arranged in a prescribed order so that the sequence of all bases is eventually determined for the nucleic acid molecule of interest.

The method and apparatus according to the present invention may be effectively used for decoding the base sequence of the nucleic acid molecule of interest with the help of reference data showing the masses of individual nucleic acids differing in base species.

The nucleic acid molecule of interest from which the reference data is generated may be an oligonucleic acid molecule or polynucleic acid molecule consisting of the same species of base (or DNA consisting only of AAAA . . . , TTTT . . . , GGGG . . . , or CCCC . . . ). This nucleic acid undergoes the first and second steps, so that data is collected about the difference in mass for each nucleic acid molecule corresponding to the species of base. This data is compared or collated with the measured (or detected) data so as to decode the base sequence of the nucleic acid molecule of interest with the help of the procedure to automatically judge the species of bases and the combination of bases.

A concrete description is given below. It is assumed that the difference in mass of each deoxyribonucleic acid molecule consisting only of A, G, C, or T is $\Delta ma$, $\Delta mg$, $\Delta mc$, or $\Delta mt$, respectively. It is also assumed that the change in mass which is measured sequentially when the nucleic acid molecule of interest (whose base sequence is unknown) is cleaved by the unit of polypeptide molecule is $\Delta ma$, $\Delta mc$, $\Delta mt$, $\Delta mg$, $\Delta mc$, and $\Delta mt$. Then it is possible to determine that the nucleic acid molecule of interest has the base sequence of "ACTGCT".

According to the present invention, the nucleic acid molecule of interest has its one end fixed to the surface of solid phase, such as quartz oscillator and piezoelectric element (surface acoustic wave device). With the help of such devices, it is possible to measure the change in mass that occurs after the first step in terms of the change in resonance frequency. In this way it is possible to decode the base sequence of the nucleic acid molecule of interest.

The present invention is directed also to an apparatus for determining the base sequence of a nucleic acid molecule, the apparatus including a unit to supply a reaction region with a substance that cleaves a nucleic acid molecule of interest in the reaction region, a unit to detect the change in mass of the nucleic acid molecule which has undergone cleavage, a unit to analyze the data detected by the detecting unit, and a unit to send out the results of analysis accomplished by the analyzing unit.

The data analyzing unit mentioned above may be so constructed as to compare the detected data with the reference data which has previously been stored for individual base species and then identify the base species of the nucleic acid molecule which has been cleaved from the nucleic acid molecule of interest. Also, the detecting unit mentioned above may be so constructed as to detect the amplitude of vibration of the cantilever which permits the nucleic acid molecule of interest to be fixed to its end surface.

Incidentally, in the present invention, the term "nucleic acid" means a nucleotide chain or a polymer of phosphate ester of nucleoside composed of purine or pyrimidine base and sugar binding to each other through the glycosidic linkage. It broadly embraces oligo- and poly-nucleotide (including probe DNA), complete or fragmented DNA composed of purine nucleotide and pyrimidine nucleotide, cDNA (c probe DNA) obtained by reverse transcription, RNA, and polyamide nucleotide derivative (PNA).

The present invention makes it possible to accurately and rapidly determine the base sequence of a nucleic acid (or nucleotide chain) by measuring its change in mass after cleavage.

DETAILED DESCRIPTION OF THE PREFERRED EMBODIMENTS

The preferred embodiments of the present invention will be described in more detail with reference to the accompanying drawings. The embodiments shown in the accompanying drawings are intended to merely illustrate the concept and typical examples of the method and apparatus according to the present invention. They should not be construed to restrict the scope of the present invention.

Figure 1:
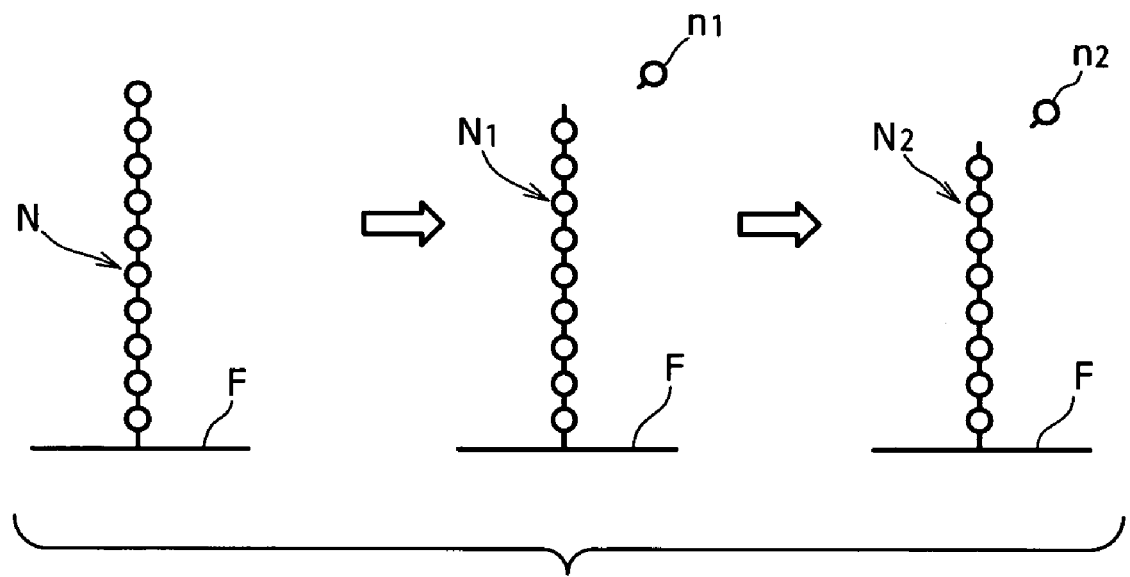
FIG. 1 is a schematic diagram illustrating the fundamental concept of the first step in the method according to the present invention.

FIG. 1 is a schematic diagram illustrating the fundamental concept of the first step in the method according to the present invention.

To carry out the first step, it is necessary to prepare a sample of the nucleic acid molecule of interest (consisting of nucleotide chain in prescribed length) such that the terminal of the nucleotide chain (N) is immobilized to the surface (F) of a solid phase (It is assumed that the nucleotide chain consists of 10 molecules for convenience' sake of illustration). Such a sample can be prepared by using any known immobilizing technique. Subsequently, the nucleic acid molecule of interest is cleaved by means of a properly selected nuclease, such that cleavage starts at a properly controlled site near the free end thereof.

Some known immobilizing techniques are explained below. The detector which is surface-treated with streptavidin is suitable to immobilize the terminal of biotinylated DNA probe. The detector which is surface-treated with thiol (SH) groups is suitable to immobilize through disulfide (—S—S—) linkage the probe DNA (to be detected) which is modified with thiol terminal groups.

The cleavage of the nucleic acid molecule of interest (which is indicated by the symbol N in FIG. 1) may be accomplished by using exonuclease (not shown) as one kind of nucleases, which cleaves nucleic acid one by one, starting at the site near the free end.

In FIG. 1, the symbol $N_1$ schematically denotes the nucleic acid residue consisting of nine molecules which remains after one nucleic acid molecule ($n_1$) at the terminal has been cleaved. The number of molecules in the residue is decreased by one from the number of molecules in the starting nucleic acid. Likewise, the symbol $N_2$ in FIG. 1 denotes the nucleic acid residue consisting of eight molecules which remains after two nucleic acid molecules ($n_2$) at the terminal have been cleaved. The number of molecules in the residue is decreased by two from the number of molecules in the preceding nucleic acid. Incidentally, the present invention does not impose specific restrictions on the number of bases (or molecules) of the nucleic acid molecule of interest (indicated by the symbol N).

The process of cleaving (or decomposing) the nucleic acid molecule of interest (N) proceeds as follows. The nucleic acid molecule of interest (N) changes in mass from its initial mass ($M_N$) to a reduced mass ($M_{N1}$), which is smaller than the initial mass by a mass equivalent to one nucleic acid ($n_1$) which has been cleaved. After the second cleavage, the first reduced mass ($M_{N1}$) changes into the second reduced mass ($M_{N2}$), which is smaller than the first reduced mass by a mass equivalent to the sum of the two nucleic acids ($n_1$ and $n_2$ which have been cleaved.

Since each nucleic acid has its inherent mass according to its constituent bases, it will be possible to determine the base species of the nucleic acid molecules ($n_1$ and $n_2$) which are produced by cleavage (or decomposition) if the difference in mass ($\Delta m$) in each step of cleavage is measured sequentially by an adequate means.

For example, in the case of DNA (or deoxyribonucleic acid) as the nucleic acid molecule of interest, the constituent bases are adenine (A), guanine (G), cytosine (C), and thymine (T). In the present invention, deoxyribonucleotide molecules as cleavage products (or decomposition products) corresponding to these base species are represented by dA, dG, dC, and dT for convenience' sake. Incidentally, these deoxyribonucleotides dA, dG, dC, and dT as cleavage products may be divided into those having the phosphate group at the 5' terminal and those having the phosphate group at the 3' terminal; however, they are not distinguished in the present invention.

If the deoxyribonucleotides dA, dG, dC, and dT are assumed to have their inherent masses MdA, MdG, MdC, and MdT, respectively, it will be possible to determine that the deoxyribonucleotide resulting from cleavage is dA if the difference in mass ($\Delta m$) measured corresponds to the inherent mass MdA.

Likewise, it will be possible to determine that the deoxyribonucleotide resulting from cleavage is dG if the difference in mass ($\Delta m$) measured corresponds to the inherent mass MdG, the deoxyribonucleotide resulting from cleavage is dC if the difference in mass ($\Delta m$) measured corresponds to the inherent mass MdC, and the deoxyribonucleotide resulting from cleavage is dT if the difference in mass ($\Delta m$) measured corresponds to the inherent mass MdT.

The nuclease used in the present invention to cleave the nucleic acid molecule of interest is not strictly restricted. It includes deoxyribonuclease that acts on single-stranded or double-stranded DNA, ribonuclease that acts on RNA, nuclease that acts on both DNA and RNA, NNase-I and NNase-II both acting mainly on double-stranded DNA and RNA, ATP-dependent NNase, RNase-III, nuclease $S_1$ that acts on single-stranded DNA and RNA, nuclease $P_1$, exoN-Nase I, RNase II, base-specific RNase $T_1$, RNase $U_2$, RNase A, T4-endonuclease, RNase H (which is considered to recognize the high-order structure of nucleic acid), RNase P, and restriction enzymes.

The above-mentioned embodiment demonstrates the method (or apparatus) for cleaving (or decomposing) the nucleic acid molecule of interest into a single nucleic acid molecule one by one. The embodiment may also be modified such that cleavage is carried to give more than one unit of nucleic acid molecule at one time. The method or means for cleaving the nucleic acid molecule of interest is not limited to nuclease; however, any method or means may be employed so long as it is capable of cleaving the nucleic acid molecule of interest of the present invention.

The second step as described below is carried out to measure the change in mass that occurs after the nucleic acid molecule of interest has undergone cleavage.

Any method or means may be employed for this step is not specifically restricted so long as it is capable of accurately measuring the change in mass of the nucleic acid molecule to be sequenced. One typical method that meets this requirement at present is by measuring the change in resonance frequency that occurs in a piezoelectric element (pressure-electricity transducer).

It is known that a crystal of quartz, Rochelle salt, tourmaline, or the like distorts when it is given a voltage that brings about electric polarization and, conversely, it generates a voltage through electric polarization when it is distorted under pressure. This phenomenon is called piezoelectric effect. Quarts ($SiO2$) is renowned for its outstanding piezoelectric characteristics, chemical properties, and thermal stability.

The piezoelectric effect mentioned above may be utilized in the following manner. A quartz plate having electrodes attached to both side thereof produces shearing vibration when it is given a voltage to distort it. After removal of applied voltage, it returns to its original state. If the applied voltage (as an alternating electric field) is synchronized with the resonance frequency of shearing vibration, then the quarts plate resonates at its characteristic frequency like an oscillator.

The quartz oscillator mentioned above decreases in frequency when a tiny object is attached to its electrode. There is a relation between the change in frequency and the weight of tiny object as represented by Sauerbrey formula (1) below. This formula indicates that the change in mass on the electrode is proportional to the change in frequency.

$$\Delta F = -\frac{2F_0^2}{A(\mu_q \rho_q)^{1/2}} \Delta m \tag{1}$$

where,
$\Delta m$ ... change in mass
$\Delta F$ ... change in fundamental frequency
$F_0$ ... fundamental frequency
A ... area of electrode
$\mu q$ ... shear stress of quarts ($2.947 \times 10^{10}$ kg m$^{-1}$ s$^{-1}$)
$\rho q$ ... density of quarts (2648 kg m$^{-3}$)

It has been confirmed that a quarts oscillator having a fundamental frequency ($F_0$) of 27 MHz decreases in frequency by 1 Hz when a tiny object is attached to the electrode (about 0.62 ng per cm$^2$). The quartz oscillator based on this principle is called a quartz-crystal microbalance (QCM). It is so sensitive as to measure even the weight of monomolecular layer absorbed onto the electrode. Therefore, in principle, it can detect so small a change in mass as one nucleic acid molecule.

The present invention employs a method or apparatus which is based on the foregoing principle. That is, the nucleic acid to be sequenced has its end previously fixed to the surface of a quartz oscillator (which corresponds to the surface (F) of a solid phase shown in FIG. 1). The change in mass ($\Delta m$) of the nucleic acid molecule is measured in terms of the change in frequency ($\Delta F$) that occurs as cleavage in the first step proceeds on the surface.

Figure 2:
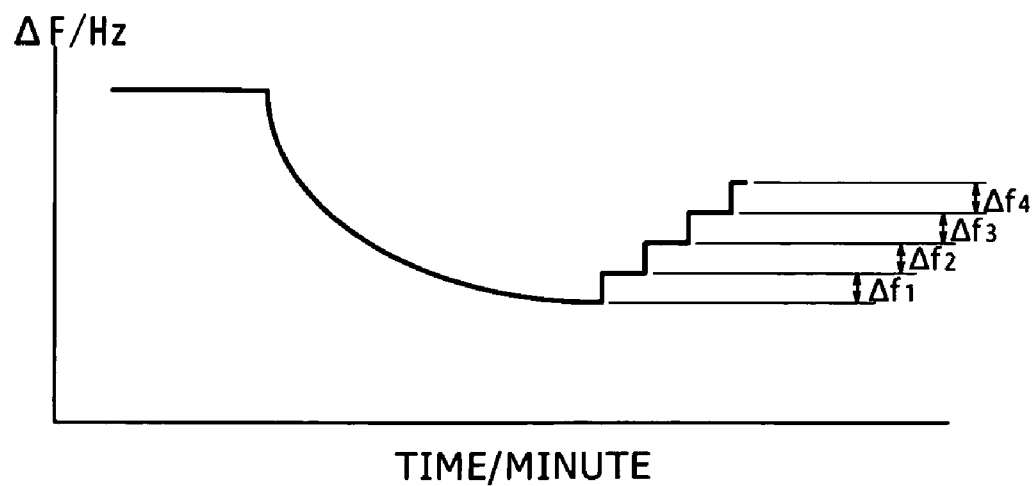
FIG. 2 is a schematic diagram illustrating the change in vibration that occurs as the nucleic acid molecule of interest is cleaved during measurement with a quartz oscillator.

In other words, the change in mass ($\Delta m$) of the nucleic acid molecule manifests itself as the change in frequency ($\Delta F$) as shown in FIG. 2. In the case of an embodiment which is designed such that the nucleic acid molecule of interest is cleaved by the unit of nucleic acid molecule, the sequentially measured change in frequency (ΔF) corresponds to the change in mass (the decrease in mass) of one nucleic acid which has been cleaved.

If it is assumed that the changes in frequency ($\Delta F_1$, $\Delta F_2$, $\Delta F_3$, and $\Delta F_4$) shown in FIG. 2 correspond to the inherent masses of the cleaved deoxyribonucleotides dA, dG, dC, and dT, then the measured data suggest the base sequence of AGCT. Incidentally, the process of acquiring the sequence information of the nucleic acid (or the cleaved deoxyribonucleotide) from the measured data corresponds to the third step in the present invention.

According to the present invention, it is possible to efficiently determine the entire base sequence of the nucleic acid molecule of interest by repeating the above-mentioned first to third steps as many times as necessary for the nucleic acid molecule of interest (oligonucleotide or polynucleotide) having a prescribed length of nucleotide chain.

The above-mentioned embodiment may be modified such that sequencing is performed on a plurality of cleaved nucleic acids in parallel at the same time. In this way it is possible to reduce time required to determine the base sequence. The base sequences of cleaved nucleic acid molecules which have been determined in this manner are eventually spliced in a certain order to determine the entire base sequence of the nucleic acid molecule of interest.

Figure 3:
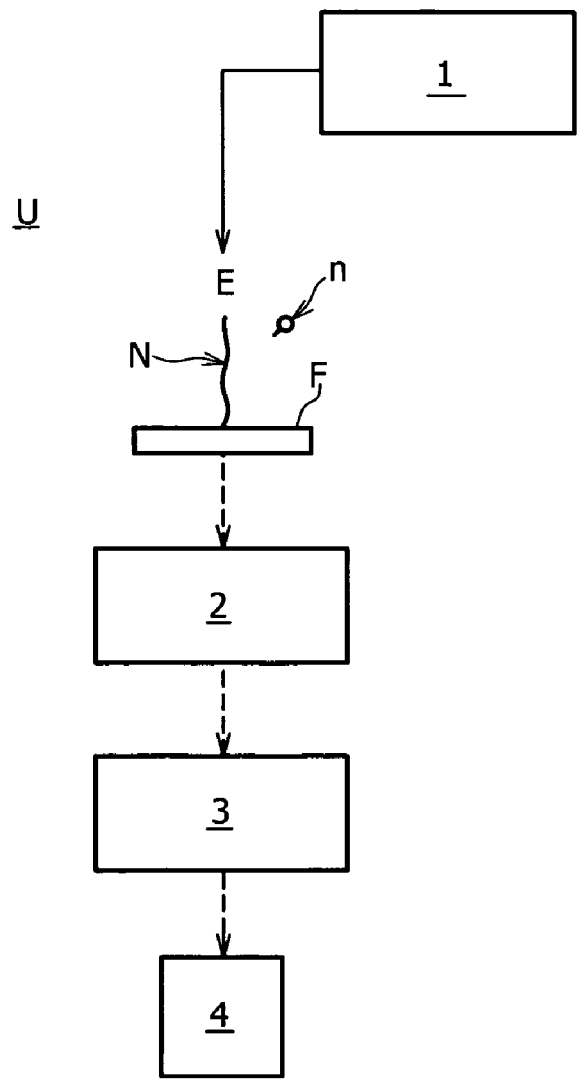
FIG. 3 is a block diagram illustrating the basic structure of the apparatus (U) according to the present invention.

FIG. 3 is a block diagram illustrating the basic structure of the sequencing apparatus (U) according to the present invention.

The sequencing apparatus (U) for determining the base sequence has at least a unit (1) to supply a reaction region (R) with a substance (E), such as a nuclease, that cleaves a nucleic acid molecule of interest (whose end is fixed to the surface of a solid phase (F)) in the reaction region, a unit (2) to detect the change in mass of the nucleic acid molecule which has undergone cleavage, a unit (3) to analyze the data detected by said detecting unit (2), and a unit (4) to send out the results of analysis accomplished by said data analyzing unit (3).

The data analyzing unit (3) compares and collates the detected data with the reference data for each base species which has previously been stored in its storage, thereby identifying the bass species of the nucleic acid molecules (n) which have been cleaved from the nucleic acid molecule of interest (N).

The reference data to be stored in the storage of the data analyzing unit (3) of the apparatus (U) may be such data as change in frequency which correlates with the change in mass of one nucleic acid molecule corresponding to each base species. Such data about the change in mass is obtained from oligonucleic acid molecules or polynucleic acid molecules composed of identical base species, which are used as the nucleic acid molecule of interest (N).

The reference data may be, for example, the change in frequency ΔFdA, ΔFdG, ΔFdC, and ΔFdT corresponding respectively to the inherent mass of deoxyribonucleotide dA, dG, dC, and dT. The reference data, which has previously been obtained, is automatically compared and collated with the measured data ($\Delta F_1$, $\Delta F_2$, $\Delta F_3$, and $\Delta F_4$) to determine the base sequence of the nucleic acid molecule of interest.

Figure 4:
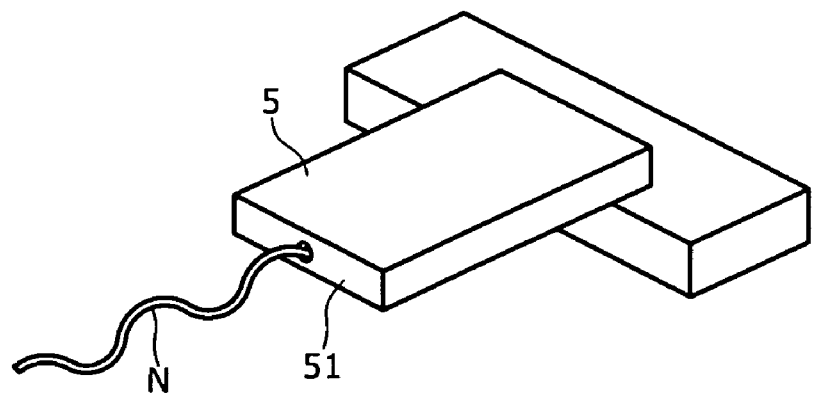
FIG. 4 is a simplified diagram illustrating the construction of the cantilever (1) that can be used for the apparatus according to the present invention.

According to the present invention, the change in mass (Δm) of the nucleic acid molecule of interest may be accomplished by using a cantilever means capable of measuring the change in characteristic frequency. A preferred cantilever (5) is shown in FIG. 4. The cantilever 5 has a piezoelectric oscillator attached to its end 51, and the surface of the oscillator is so constructed as to immobilize the nucleic acid molecule of interest. The cantilever (5) is also provided with a driving source (not shown) to excite its vibration and a detecting unit (2) (as shown in FIG. 3) to detect the amplitude of its vibration.

The cantilever (5) is excited by the driving source (or AC source) whose frequency is sequentially varied. The current corresponding to the resonance amplitude is converted into voltage produced by resistance and the voltage is read by a voltmeter (not shown). The resonance amplitude of the cantilever (5) reaches the maximum when the frequency of the AC source coincides with the characteristic frequency of the cantilever (5).

Incidentally, the cantilever may be formed from a ferroelectric substance, such as lead zirconate titanate (PZT) and strontium bismuth tantalate (SBT), which has the piezoelectric properties.

The present invention will be applied to the technique (including method, apparatus, and system) to determine the base sequence of nucleic acid molecules (nucleotide chains).

What is claimed is:

1. A method for determining the base sequence of a nucleic acid molecule, wherein the nucleic acid molecule is immobilized on a cantilever comprising a piezoelectric element, said method comprising
    a) measuring the frequency of vibration of the piezoelectric element;
    b) cleaving the nucleic acid molecule;
    c) measuring the frequency of vibration of the piezoelectric element; and
    d) determining the sequence of the nucleic acid molecule by comparing the frequency measured in a) with the frequency measured in c).

2. The method of claim 1, wherein are repeated to determine the entire base sequence of the nucleic acid molecule.

3. The of claim 1, wherein a) employs at least a nuclease.

4. The method of claim 3, wherein the nuclease is an exonuclease.

5. The method of claim 1, wherein the nucleic acid molecule is single-stranded.

6. The method for determining the base sequence of claim 1, wherein b) comprises cleaving a single nucleotide from the nucleic acid molecule.

7. The method of claim 1, wherein the nucleic acid molecule of b) comprises a portion of a larger nucleic acid molecule that has been fragmented.

8. The method for determining the base sequence of claim 7, wherein the base sequences of multiple portions of a larger nucleic acid molecule that has been fragmented are determined in parallel.

9. The method of claim 1, wherein a-c are performed on oligonucleic or polynucleic acid molecules comprising identical bases to determine the mass of each base.

10. The method of claim 1, wherein the piezoelectric element is a quartz oscillater.

11. The method of claim 1, wherein the nucleic acid molecule is biotinylated and immobilized on a cantilever comprising streptavidin.

12. The method of claim 3, wherein the nuclease is selected from deoxyribonuclease, ribonuclease, NNase-I, NNase-II, ATP-dependent NNase, RNase-III, nuclease $S_1$, nuclease $P_1$, exoNNase I, RNase II, RNase $T_1$, RNase $U_2$, RNase A, T4-endonuclease, RNase H, RNase P, and restriction enzymes.

13. The method of claim 1, wherein the cantilever comprises a ferroelectric substance.

14. The method of claim 13, wherein the ferroelectric substance is selected from lead zirconate titanate (PZT) and strontium bismuth tantalate (SBT).

* * * * *

UNITED STATES PATENT AND TRADEMARK OFFICE
CERTIFICATE OF CORRECTION

PATENT NO. : 7,371,532 B2  
APPLICATION NO. : 11/231998  
DATED : May 13, 2008  
INVENTOR(S) : Takayoshi Mamine et al.

It is certified that error appears in the above-identified patent and that said Letters Patent is hereby corrected as shown below:

Title page, col. 1, item (65), under "Foreign Application Priority Data", "P2004-281000" should read --2004-281000--.

Claim 3, col. 8, line 41, "The of claim 1" should read --The method of claim 1--.

Claim 10, col. 8, line 61, "oscillater" should read --oscillator--.

Signed and Sealed this

Tenth Day of February, 2009

JOHN DOLL  
*Acting Director of the United States Patent and Trademark Office*